(12) United States Patent
Frank et al.

(10) Patent No.: US 9,855,231 B2
(45) Date of Patent: *Jan. 2, 2018

(54) METHODS AND COMPOSITIONS FOR TREATING RAYNAUD'S DISEASE

(71) Applicant: Nexmed Holdings, Inc., San Diego, CA (US)

(72) Inventors: Daniel W. Frank, Broomall, PA (US); Richard Martin, San Diego, CA (US); Bassam B. Damaj, San Diego, CA (US)

(73) Assignee: NEXMED HOLDINGS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/224,098

(22) Filed: Jul. 29, 2016

(65) Prior Publication Data

US 2016/0331761 A1  Nov. 17, 2016

Related U.S. Application Data

(63) Continuation of application No. 14/591,487, filed on Jan. 7, 2015, now Pat. No. 9,517,218, which is a continuation of application No. 14/110,348, filed as application No. PCT/US2012/032577 on Apr. 6, 2012, now Pat. No. 8,940,794.

(60) Provisional application No. 61/472,988, filed on Apr. 7, 2011.

(51) Int. Cl.

| | |
|---|---|
| *A61K 31/201* | (2006.01) |
| *A61K 31/191* | (2006.01) |
| *A61K 9/00* | (2006.01) |
| *A61K 47/10* | (2017.01) |
| *A61K 47/12* | (2006.01) |
| *A61K 47/36* | (2006.01) |
| *A61K 31/5575* | (2006.01) |
| *A61K 47/18* | (2017.01) |
| *A61J 1/05* | (2006.01) |

(52) U.S. Cl.
CPC .............. *A61K 31/191* (2013.01); *A61J 1/05* (2013.01); *A61K 9/0014* (2013.01); *A61K 31/201* (2013.01); *A61K 31/5575* (2013.01); *A61K 47/10* (2013.01); *A61K 47/12* (2013.01); *A61K 47/18* (2013.01); *A61K 47/36* (2013.01)

(58) Field of Classification Search
None
See application file for complete search history.

(56) References Cited

U.S. PATENT DOCUMENTS

| | | |
|---|---|---|
| 4,029,814 A | 6/1977 | Bundy |
| 4,212,987 A | 7/1980 | Axen |
| 4,311,707 A | 1/1982 | Birnbaum et al. |
| 4,820,732 A | 4/1989 | Shell et al. |
| 4,955,878 A | 9/1990 | See et al. |
| 4,980,378 A | 12/1990 | Wong et al. |
| 5,082,866 A | 1/1992 | Wong et al. |
| 5,252,605 A | 10/1993 | Veno |
| 5,403,867 A | 4/1995 | Okumura et al. |
| 5,464,868 A | 11/1995 | Frolich et al. |
| 5,942,545 A | 8/1999 | Samour et al. |
| 5,952,006 A | 9/1999 | Drizen et al. |
| 6,046,244 A | 4/2000 | Buyuktimkin et al. |
| 6,118,020 A | 9/2000 | Buyuktimkin et al. |
| 6,323,241 B1 | 11/2001 | Yeager et al. |
| 6,414,028 B1 | 7/2002 | Buyuktimkin et al. |
| 6,486,207 B2 | 11/2002 | Yeager et al. |
| 6,825,234 B2 | 11/2004 | Yeager et al. |
| 7,105,571 B2 | 9/2006 | Yeager et al. |
| 7,105,572 B2 | 9/2006 | Sato |
| 8,632,813 B2 | 1/2014 | Wen et al. |
| 8,940,794 B2 | 1/2015 | Frank et al. |
| 2002/0165122 A1 | 11/2002 | Heaton et al. |
| 2005/0009918 A1 | 1/2005 | Wen et al. |
| 2005/0181030 A1 | 8/2005 | Mo et al. |
| 2006/0148907 A1 | 7/2006 | Nicholson et al. |
| 2008/0069883 A1 | 3/2008 | Wen et al. |
| 2009/0252685 A1 | 10/2009 | Yu et al. |

FOREIGN PATENT DOCUMENTS

| | | |
|---|---|---|
| CA | 2442479 A | 11/2000 |
| EP | 0 292 643 A | 11/1988 |
| EP | 0 503 887 A2 | 9/1992 |
| EP | 1 178 833 B1 | 8/2004 |
| JP | S63-246331 | 10/1988 |
| JP | 2002-544240 A | 12/2002 |
| WO | WO-95/09590 A1 | 4/1995 |

(Continued)

OTHER PUBLICATIONS

Scheffler et al., "Effects of Intravenous PGE1 on Blood Flow and Microcirculation: A Double-Blind, Placebo-Controlled Study in Patients with Critical Limb Ischaemia", Prostaglandin E1, 1991, pp. 91-100.

(Continued)

*Primary Examiner* — Samantha Shterengarts

(74) *Attorney, Agent, or Firm* — Foley & Lardner LLP

(57) ABSTRACT

In various embodiments, methods and compositions for treating Raynaud's disease and Raynaud's phenomenon are provided. Topical administration of a semisolid composition comprising a prostaglandin $E_1$ compound provides the desired relief of the Raynaud's disease or Raynaud's phenomenon without the possible complications of systemic administration. The semisolid composition can be administered as needed, or in a regimen of several doses per day.

8 Claims, 1 Drawing Sheet

(56) References Cited

FOREIGN PATENT DOCUMENTS

| WO | WO-99/22714 | 5/1999 |
| WO | WO-00/69469 A1 | 11/2000 |
| WO | WO-2004/089381 A1 | 10/2004 |
| WO | WO-2009/036311 | 3/2009 |
| WO | WO-2012/139033 A1 | 10/2012 |

OTHER PUBLICATIONS

U.S. Appl. No. 14/110,348, filed Oct. 7, 2013, Nexmed Holdings, Inc.
U.S. Appl. No. 14/154,892, filed Jan. 14, 2014, Nexmed Holdings, Inc.
U.S. Appl. No. 14/172,591, filed Feb. 4, 2014, Nexmed Holdings, Inc.
U.S. Appl. No. 14/173,660, filed Feb. 5, 2014, Nexmed Holdings, Inc.
"Acrocyanosis" in Merck Manual of Medical Information—Second Home Edition Online Edition atwww.merck.com/mmge/sec07/ch080b. 2004-2008.
"Peripheral Arterial Disease" in Merck Manual of Medical Information—Second Home Edition Online Edition at www.merck.com/mmge/sec07/ch080/ch080f. 2004-2008.
"Peripheral vascular disease" in Online Medical Dictionary at www.cancerweb.ncl.ac.uk/cgi-bin/omd?query=peripheral+vascular+disease. 1997-2000.
"Raynaud's Phenomenon" in Merck Manual of Medical Information—Second Home Edition Online Edition.at www.merck.com/mmpe/sec07/ch080/ch080g. 2004-2008.
"vasospasm" in Online Medical Dictionary at www.cancerweb.ncl.ac.uk/cgi-bin/omd?query=vasospasm. 1997-2007.
Buncke, H.J., "Microsurgery: Transplantation-Replantation," on-line edition, chapter 36, http://buncke.orgltextbook.html, accessed Dec. 13, 2002.
Buyuktimkin, et al., "Chemical Means of Transdermal Drug Permeation Enhancement." In Transdermal and Topical Drug Delivery Systems, Tapash K. Ghosh et al., eds. (IL: Interpharm Press), (1997), 357-475.
Clifford, et al., "Treatment of vasospastic disease with prostaglandin E1," British Medical Journal, (1980), 281:1031-1034.
Coffman, "Raynaud's phenomenon. An update," Hypertension, (1991), 17:593-602.
Cragg, et al., "Vessel wall arachidonate metabolism after angioplasty," Am J Cardiol, (1983), 51:1441-1445.
Definition of "replantation," p. 1445, Dorland's Illustrated Medical Dictionary, 28 Ed., W. B.Saunders Co., Philadelphia 1994.
Eskitascioglu, et al., "The effects of topical prostacyclin and prostaglandin E1 on flap survival after nicotine application in rats," Ann Plast. Surg., (2005), 55(2):202-206.
Extended European Search Report dated Oct. 19, 2014 for EP Patent Application Serial No. 12 767 469.5.
Guyatt et al., "Evidence Based Medicine. A New Approach to Teaching the Practice of Medicine" JAMA, (1992), 268(17):2420-2415.
Guyatt, et al., "Users' Guides to the Medical Literature II How to Use an Article About Therapy or Prevention. A. Are the Results of the Study Valid?" JAMA, (1993), 270(21):2598-2601.
Guyatt, et al., "Users' Guides to the Medical Literature. II. How to Use an Article About Therapy or Prevention. B. What are the Results and Will They Help Me in Caring for My Patients?" JAMA, (1994), 270(21):59-63.
Hong, et al. "The effect of prostaglandin E1 versus ischemia-reperfusion injury of musculocutaneous flaps," Ann Plast. Surg.,(2001), 47(3):316-321.
International Search Report from PCT/US2012/32577 dated Jul. 11, 2012.
Katoh et al., "Use of prostaglandin el (Lipo-PGE1) to treat Raynaud's phenomenon assocaited with connective tissue disease: thermographic and subjective assessments", J.Pharm. Pharmacol. (1992) 44:442-444.
Kuwahara et al., "The effects of lipo-prostaglandin El on axial pattern flaps in rabbits," Ann Plast. Surg., (1995), 35(6):620-266.
Langevitz et al., "Treatment of refractory ischemic skin ulcers in patients with Raynaud's phenomenon with PGE1 infusions", J Rheumatol., 1989, 16(11):1433-5. (Abstract Only).
Mizushirna et al., "Prostaglandin El is more effective, when incorporated in lipid microspheres, for treatment of peripheral vascular diseases in man," Journal of Pharmacology, (1983), 35(10):666-667.
Mohrland et al., "A multiclinic, placebo-controlled, double-blind study of prostaglandin El in Raynaud's syndrome," Annals of the Rheumatic Diseases, (1985), 44:754-760.
Nakanishi et al., "The transepidermal absorption of prostaglandin El as a topical ointment: an experimental study of application over a rat skin flap," Ann Plast Surg., (1998), 40(1):44-47.
Novotny et al., "Dimethylamino acid esters as biodegradable and reversible transdermal permeation enhancers: effects of linking chain length, chirality and polyfluorination", Pharm. Res., 2009, 26(4):811-21, Abstract [online] (found in the Internet: http://www.ncbi.nlm.nih.gov/pubmed/19009336).
Oxford-Centre for Evidence-Based Medicine, "Levels of Evidence and Grades of Recommendation," web page archived cm Jun. 21, 2003, retrieved from tbe Internet Archive Vv'ayBack Machine on Apr. 22, 2012, hHp://web.archi ve.org/webi20030621 165628/ http://www.cebm.net/levels_of_evidence.asp[Apr. 22, 2012 3:30:1 4 PM I.
Oxman, et al., "Users' Guides to the Medical Literature. 1. How to Get Started," JAMA, (1993), 270(17):2093-2095.
Pope et al., "Iloprst and cisaprost for Raynaud's phenomenon in progressive systemic sclerosis," Cochrane Database Syst Rev. 1998, Issue 2. ArL No. CD000953. Reprinted in 2009 and published by John Wiley & Sons, Ltd.
Sakai et al., "Prostaglandin E2 regulates the expression of basic fibroblast growth factor messenger RNA in normal human fibroblasts," Kobe J. Med. Sci. (2001), 47:35-45.
Sawada et al. "A study of topical and systemic prostaglandin El and survival of experimental skin flaps," Br J Plast. Surg., (1993), 46(8):670-672.
Sawada et al., "A new system of treating wounds by a continuous topical application of medication," Br J Plast Surg., (1990), 43(1):83-87.
Schlez et al., "Transdermal application of prostaglandin El ethyl ester for the treatment of trophic acral skin lesions in a patient with systemic scleroderma", Journal of the European Academy of Dermatology and Venereology, 2002, 16(5): 526-528.
Schlez et al., "Verbesserung der Hautdurchblutung durch die transdermale Applikation von PGE1-Ethylesther bei systemischer Sklerodermie", VASA, 2015, Zeitschrift fur Gefasskrankheiten, 32, pp. 83-86. Abstract Only.
Shanz et al., "Topical treatment of erectile dysfunction with prostaglandin E1 ethyl ester", JDDG: Journal der Deutschen Dermatologischen Gesellschaft, 2009, 7(12): 1055-1059.
Slodicke et al. "Die Anwendung von Prostaglandin E1 bei mikrovasculiiren Rekonstruktion der oberen Extremitiit nach Akut-traumen, (Using Prostaglandin E1 in microvascular reconstruction of the upper extremity after acute trauma)," Unfallchirurg, Jan; 105(1): 14-8 (2002). (English abstract on p. 15).
Smalling et al., "Infarct salvage with liposomal prostaglandin E-1 administered by intravenous bolus immediately before reperfusion in a canine infarction-reperfusion model," Circulation, (1995), 92(4):935-943.
Systemic Scleroderma Clinical Practice Guidelines, Scleroderma Search and Research Group Secretariat, Oct. 2010, p. 71 to 80.
Verma et al., "Fundamentals of reperfusion injury for the clinical cardiologist", Journal of the American Heart Association, (2002), 105:2332-2336.
Zollikofer et al., "Prostaglandins and angioplasty. An experimental study in canine arteries," Radiology, (1983), 149(3):681-685.

«METHODS AND COMPOSITIONS FOR TREATING RAYNAUD'S DISEASE»

CROSS-REFERENCE TO RELATED APPLICATIONS

This application is a Continuation Application under 35 U.S.C. §120 of U.S. patent application Ser. No. 14/591,487, which was filed on Jan. 7, 2015; which is a Continuation Application under 35 U.S.C. §120 of U.S. patent application Ser. No. 14/110,348, having a 371(c) acceptance date of Mar. 13, 2014, now U.S. Pat. No. 8,940,794, issued on Jan. 27, 2015; which claims priority under 35 U.S.C. §371 to International Patent application No. PCT/US2012/032577, filed on Apr. 6, 2012; which claims priority to U.S. Provisional Application No. 61/472,988, filed on Apr. 7, 2011; all of which are incorporated herein by reference in their entirety.

FIELD OF THE INVENTION

The present invention relates to methods and compositions for the treatment of Raynaud's disease and Raynaud's phenomenon.

BACKGROUND OF THE INVENTION

Raynaud's disease (RD) and Raynaud's phenomenon (RP) are disorders having a prevalence of about 3% to more than 5% that affect peripheral blood vessels, involving brief episodes of vasospasm causing decreased blood flow to the fingers and toes, and rarely to the nose, ears, nipples, and lips. When this disorder occurs without any known cause, it is called Raynaud's disease, or primary Raynaud's. When the condition occurs along with a likely cause, it is known as Raynaud's phenomenon, or secondary Raynaud's. Raynaud's disease, most common in young women (60 to 90% of reported cases), is idiopathic. Raynaud's phenomenon is secondary to other conditions, such as connective tissue disorders, obstructive arterial diseases (arteriosclerosis obliterans, thromboangiitis obliterans, thoracic outlet syndrome), neurogenic lesions, drug intoxications (ergot, methysergide), dysproteinemias, myxedema, primary pulmonary hypertension, and trauma. Raynaud's phenomenon is commonly found associated with certain rheumatic diseases such as systemic sclerosis, systemic lupus erythematosus, and rheumatoid arthritis. Secondary Raynaud's may also be a result of mechanical trauma, hand-arm vibration syndrome, paraprotinemias, and certain chemicals. Patients with secondary Raynaud's associated with rheumatic diseases often have autoantibodies such as a +ANA, +anti-centromere, and/or +anti-scl-70, and visible changes in their nailfold capillary pattern. As used herein, "Raynaud's" when used without a noun encompasses both Raynaud's disease and Raynaud's phenomenon.

Cold temperatures or stressful emotions can trigger attacks of either primary or secondary Raynaud's. In response to cold exposure, vasospasm in distal arteries and arterioles leads to blood being shunted from the extremities through the numerous arteriovenous anastomoses found in the digits. In response to heat, flow is decreased through these anastamoses and instead capillary flow is increased. The classical pattern consists of triphasic color changes of white (ischemia), blue or purple (cyanosis or deoxygenation), and red (reperfusion phase). The affected areas can throb or feel numb and tingly. With severe Raynaud's, prolonged or repeated episodes can cause prolonged pain, sores or tissue death (gangrene).

Since stressful emotions can trigger attacks of either primary or secondary Raynaud's, a central nervous system component is indicated as well as a peripheral vascular component.

There is no accepted standard method of measuring the severity of the disease or response to therapy. The attacks of Raynaud's are difficult to elicit, and the severity of the elicited attacks varies. Since many patients do not develop the full triphasic color changes, there is some controversy over proper diagnosis of the condition. In addition, complaints of sensation changes (cold, numbness, tingling, or pain) vary among patients these changes do not strictly correlate with the observed color differences.

Many different classes of drugs have been used to treat patients with Raynaud's. Much work has focused on vasodilators. Calcium channel blockers are the most commonly used class of vasodilators, and have been shown to be effective in several studies. However, many patients do not respond or cannot tolerate these drugs because of frequent adverse effects such as headache, flushing, and hypotension. Some studies have been carried out on other drugs that can improve vasodilation including angiotensin-II type I receptor antagonist, topical nitrates, serotonin antagonists, non-selective endothelin receptor antagonist, and phosphodiesterase inhibitors.

Studies have shown that the potent vasodilators, prostaglandins and prostacyclin analogs, are beneficial for treating severe Raynaud's. Unfortunately, prostaglandins and prostacyclin analogs are typically administered via intravenous infusion, necessitating hospitalization for their use. A few studies have examined the use of oral prostacyclin analogs, but mixed results have been reported with one study showing benefit, another showing no benefit over placebo. There have been only a few studies on the use of topical agents directly applied to the hands for the treatment of Raynaud's, and while some compositions have included prostanoids, most have involved nitrate compounds, such as glyceryl trinitrate, or minoxidil.

The prostacyclin analogue iloprost has been effective in secondary Raynaud's associated with scleroderma. alprostadil has been shown to be as effective as iloprost in a blind study, and was reported to improve severe digital ischemia associated with severe Raynaud's in another study. The prostanoids have been reported to have other effects besides vasodilation, including decreasing endothelial injury markers, which may imply an effect on reducing structural damage of vessel walls, decreasing neutrophil activation, inhibiting platelet aggregation, and modulating fibrinolytic activity. These agents may therefore have longer-term beneficial effects than that expected from their immediate vasodilatory effect. There have been reports of sustained benefit from use of these drugs; effects from a transdermal patch of $PGE_2$ were reported to last at least 84 hours, and intravenous infusions of these agents have been reported to last from 30 days to 12 weeks.

SUMMARY OF THE INVENTION

In various embodiments, methods and compositions for treating Raynaud's disease and Raynaud's phenomenon are provided. Topical administration of a semisolid composition comprising a prostaglandin $E_1$ compound provides the desired relief of the Raynaud's disease or Raynaud's phenomenon without the possible complications of systemic administration. The semisolid composition can be administered as needed, or in a regimen of several doses per day.

In certain embodiments, a method of treating Raynaud's disease and Raynaud's phenomenon in a subject is provided, comprising the steps of providing a semisolid composition comprising a prostaglandin $E_1$ compound and applying an effective amount of the semisolid composition to the surface of an affected body part. In certain embodiments, the semisolid composition comprises a prostaglandin $E_1$ compound selected from the group consisting of prostaglandin $E_1$, $C_1$-$C_4$ esters of prostaglandin $E_1$, and pharmaceutically acceptable salts thereof; a thickening agent selected from a polysaccharide gum, a chemically modified polysaccharide gum; a skin penetration enhancer that is selected from an N,N-di($C_1$-$C_8$) alkylamino substituted ($C_4$-$C_{18}$) alkyl ($C_2$-$C_{18}$) carboxylic ester and pharmaceutically acceptable acid addition salts thereof; and a ($C_1$-$C_4$)-alkyl ($C_8$-$C_{22}$) carboxylic ester. In some embodiments, the N,N-di($C_1$-$C_8$) alkylamino substituted ($C_4$-$C_{18}$) alkyl ($C_2$-$C_{18}$) carboxylic ester is selected from the group consisting of dodecyl-2-(N,N-dimethylamino)-propionate; dodecyl-2-(N,N-dimethylamino)-acetate; 1-(N,N-dimethylamino)-2-propyl dodecanoate; 1-(N,N-dimethylamino)-2-propyl myristate; 1-(N,N-dimethylamino)-2-propyl oleate; and pharmaceutically acceptable acid addition salts thereof. In certain embodiments, the semisolid composition is supplied in a unit dose dispenser. Preferably, the semisolid composition is at room temperature when applied to the surface of the affected body part to avoid triggering or exacerbating the vasospasm that is characteristic of Raynaud's disease or Raynaud's phenomenon. In certain embodiments, the semisolid composition is stored at room temperature. In some embodiments, the semisolid composition is provided in a two-part unit dose container. In preferred embodiments, the total daily dose of a prostaglandin $E_1$ compound that is applied to the surface of the affected body part is about 0.5 to about 5.7 mg. In some embodiments the total daily dose is divided into 2-4 doses and is administered in a regimen of separate applications over the course of 12-24 hours. In a preferred embodiment, three doses are applied daily. Typically, the affected body parts are the extremities, the hands and/or the feet. In certain embodiments, the total daily dose is applied to both hands, or to a single hand, depending on the affected area and the severity of the condition.

In other embodiments, a pharmaceutical composition is provided that comprises a prostaglandin $E_1$ compound for use in a treatment of Raynaud's disease or Raynaud's phenomenon by the topical administration of the composition to the surface of an affected body part. In certain embodiments, the pharmaceutical composition comprises a prostaglandin $E_1$ compound selected from the group consisting of prostaglandin $E_1$, $C_1$-$C_4$ esters of prostaglandin $E_1$, and pharmaceutically acceptable salts thereof; a thickening agent selected from a polysaccharide gum, a chemically modified polysaccharide gum; a skin penetration enhancer that is selected from an N,N-di($C_1$-$C_8$) alkylamino substituted ($C_4$-$C_{18}$) alkyl ($C_2$-$C_{18}$) carboxylic ester and pharmaceutically acceptable acid addition salts thereof; and a ($C_1$-$C_4$-alkyl ($C_8$-$C_{22}$) carboxylic ester. In some embodiments, the N,N-di($C_1$-$C_8$) alkylamino substituted ($C_4$-$C_{18}$) alkyl ($C_2$-$C_{18}$) carboxylic ester is selected from the group consisting of dodecyl-2-(N,N-dimethylamino)-propionate; dodecyl-2-(N,N-dimethylamino)-acetate; 1-(N,N-dimethylamino)-2-propyl dodecanoate; 1-(N,N-dimethylamino) -2-propyl myristate; 1-(N,N-dimethylamino) -2-propyl oleate; and pharmaceutically acceptable acid addition salts thereof. In certain embodiments, the pharmaceutical composition is supplied in a unit dose dispenser. Preferably, the pharmaceutical composition is at room temperature when applied to the surface of the affected body part to avoid triggering or exacerbating the vasospasm that is characteristic of Raynaud's disease or Raynaud's phenomenon. In certain embodiments, the pharmaceutical composition is stored at room temperature. In some embodiments, the pharmaceutical composition is provided in a two-part unit dose container. In preferred embodiments, the total daily dose of a prostaglandin $E_1$ compound that is applied to the surface of the affected body part is about 0.5 to about 5.7 mg. In some embodiments the total daily dose is divided into 2-4 doses and is administered in a regimen of separate applications over the course of 12-24 hours. In a preferred embodiment, three doses are applied daily. Typically, the affected body parts are the extremities, the hands and/or the feet. In certain embodiments, the total daily dose is applied to both hands, or to a single hand, depending on the affected area and the severity of the condition.

In other embodiments, the use of a prostaglandin $E_1$ compound for the manufacture of a semisolid pharmaceutical composition for the treatment of Raynaud's disease or Raynaud's phenomenon is provided, wherein the Raynaud's disease or Raynaud's phenomenon is treated by the topical administration of the semisolid pharmaceutical composition to the surface of an affected body part. In certain embodiments, the semisolid pharmaceutical composition comprises a prostaglandin $E_1$ compound selected from the group consisting of prostaglandin $E_1$, $C_1$-$C_4$ esters of prostaglandin $E_1$, and pharmaceutically acceptable salts thereof; a thickening agent selected from a polysaccharide gum, a chemically modified polysaccharide gum; a skin penetration enhancer that is selected from an N,N-di($C_1$-$C_8$) alkylamino substituted ($C_4$-$C_{18}$) alkyl ($C_2$-$C_{18}$) carboxylic ester and pharmaceutically acceptable acid addition salts thereof; and a ($C_1$-$C_4$)-alkyl ($C_8$-$C_{22}$) carboxylic ester. In some embodiments, the N,N-di($C_1$-$C_8$) alkylamino substituted ($C_4$-$C_{18}$) alkyl ($C_2$-$C_{18}$) carboxylic ester is selected from the group consisting of dodecyl-2-(N,N-dimethylamino)-propionate; dodecyl-2-(N,N-dimethylamino)-acetate; 1-(N,N-dimethylamino)-2-propyl dodecanoate; 1-(N,N-dimethylamino)-2-propyl myristate; 1-(N,N-dimethylamino)-2-propyl oleate; and pharmaceutically acceptable acid addition salts thereof. In certain embodiments, the semisolid composition is supplied in a unit dose dispenser. Preferably, the semisolid pharmaceutical composition is at room temperature when applied to the surface of the affected body part to avoid triggering or exacerbating the vasospasm that is characteristic of Raynaud's disease or Raynaud's phenomenon. In certain embodiments, the semisolid pharmaceutical composition is stored at room temperature. In some embodiments, the semisolid pharmaceutical composition is provided in a two-part unit dose container. In preferred embodiments, the total daily dose of a prostaglandin $E_1$ compound that is applied to the surface of the affected body part is about 0.5 to about 5.7 mg. In some embodiments the total daily dose is divided into 2-4 doses and is administered in a regimen of separate applications over the course of 12-24 hours. In a preferred embodiment, three doses are applied daily. Typically, the affected body parts are the extremities, the hands and/or the feet. In certain embodiments, the total daily dose is applied to both hands, or to a single hand, depending on the affected area and the severity of the condition.

DETAILED DESCRIPTION OF THE INVENTION

Measurement Techniques

Figure 1:
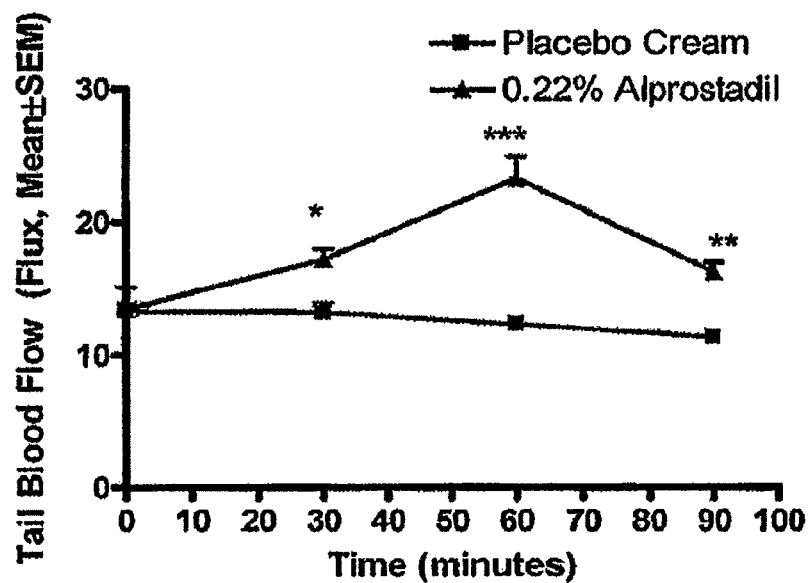
FIG. 1 is a graphical representation of the results of a study of the effects of a topical prostaglandin composition on peripheral blood flow in response to a 16° C. cold challenge in an animal model.

Since the primary problem in Raynaud's is vasoconstriction of arteries and arterioles in the digits, with shunting of blood-flow away from the digits, various methods have been used to measure blood flow. These methods include plethysmography, laser Doppler flowmetry (LDF), laser Doppler imaging (LDI), temperature measurements (direct digital and thermography), and Doppler ultrasonography. There is often significant individual variability, with the range of values found for normal subjects generally overlapping the range found in Raynaud's. There is also a concern that methods such as plethysmography, laser Doppler flowmetry, direct digital temperature reading, and Doppler ultrasound that require direct patient contact with the test device may disturb the patient's circulation. Additionally, it is difficult to ensure precise, reproducible probe placement, some of these methods have the additional issue of reproducibility if multiple readings are required from the same subject. In contrast, LDI and thermography allow a larger area to be examined, and do not involve direct patient contact, allowing more data to be collected, and minimizing variability related to direct patient contact or probe placement. While the flux gradient of LDI may correlate poorly with the temperature gradient measured by thermography, both methods are felt to provide useful information. Patient report measures that are commonly used include diaries of attacks, noting frequency, severity, trigger, and duration, and a visual analogue scale (VAS) to note pain or severity, as well as general state of their disease.

Skin temperature, as an indirect measure of blood flow, can be affected by both intrinsic and extrinsic factors. Thermography should be done in a temperature and humidity controlled room to minimize the effects of these factors on measurements. Large intra-patient variability can be found when the same patient is assayed at different times; and an internal comparison (ratio between distal to proximal points, or comparison between treated and placebo hands) can be used as the measure of effect.

Thermography has shown that patients with Raynaud's have a lower baseline skin temperature than normal subjects. Female Raynaud's patients have also been reported to have an even lower baseline than males. Several treatment studies have found that a 2° C. or greater change in baseline temperature represents a significant change. Studies have reported a significant increases in mean skin temperature after intravenous administration of calcitonin gene related peptide (CGRP), $PGI_2$, and $PGE_1$, oral or sublingual nifedipine or application of nitroglycerine tape (NTG) placement on the wrist of patients.

Several investigators have used thermography to show that recovery from a cold challenge test is abnormal in patients with Raynaud's, with a lag in the onset of rewarming, delay in the rate of recovery, and lower temperature achieved at a set point after a cold challenge. The pattern of rewarming can also be different, with normal subjects showing rewarming beginning from the finger pulps and spreading proximally, while patients with Raynaud's have rewarming beginning at the base of the fingers and spreading distally. A two-fold increase in rewarming was seen 10 minutes into a CGRP, while a smaller, but still significant improvement in rewarming was found with fluoxetine.

Laser Doppler flowmetry (LDF): and laser Doppler imaging (LDI) measure moving particle density and flux, with flux used to represent blood flow. The light can penetrate about 1 mm, which permits measurements from superficial nutritional capillaries and deeper thermoregulatory vessels using different wavelengths of light. LDF requires direct contact with the study target, making it difficult to compare different sites with each other because of large variations in flux with even small positional changes, and significant intra individual variability has been found. LDI allows the entire hand to be scanned, minimizing variability between sites, but only a small number of studies have used this technique. As units reported for LDI are arbitrary, it best serves in comparison studies rather than for generating absolute standard values. A good correlation has been found between LDF and LDI.

LDI has been used to assess the effect of topical glyceryl trinitrate (GTN) on finger flow in comparison to petroleum jelly or no treatment. A significant increase in flow has been reported immediately and ten minutes after topical GTN application. A significant increase in digital blood flow as measured by LDF has been reported after treatment with vardenafil. Application of a nitric oxide-generating cream to finger pulps, LDF has been reported to significantly increase flux. Removal of the gel showed a decrease in flux, but still a significant difference between NO cream and placebo. Sublingual nifedipine also has been reported to produce an increase in flux compared to placebo. Intravenous $PGI_2$ has been reported to cause an increase in LDF. A CGRP infusion caused an increase LDF, along with flushing of face and hands.

Since Raynaud's attacks are typically precipitated by cold exposure, many investigators have used cold challenges to try to elicit attacks or findings typically found in attacks. However, researchers differ in their cold challenge methodology, with a range of temperatures used (0° C., 10° C., 12° C., 15° C., 16° C., 20° C., for different durations of about 1 to 10 minutes. Most studies use a temperature of 15 or 16° C. for 1 minute. The patient is asked to put on a thin glove that fits well, such as a latex glove, avoiding a tight fit as well as an overly loose fit that would trap air around the subject's hand. The hand is then lowered into a water bath at the specified temperature for the specified time. Some studies have specified lowering to the mid metacarpal level. After removal from the water bath, the gloves are removed, and the study measures assayed. Temperatures and/or flow are typically measured for 10-20 minutes after the cold challenge. There is significant inter individual difference, but the method is felt to be useful for therapeutic studies.

The Compositions

Suitable topical prostaglandin compositions for the practice of preferred embodiments of the present invention are disclosed in U.S. Pat. Nos. 6,046,244, 6,118,020, 6,323,241 and 6,841,574, the entire contents of which are incorporated by reference herein.

In one preferred embodiment, the prostaglandin E composition comprises about 0.025 percent to about 40 percent by weight of a thickening agent (e.g., guar gum); about 0.025 percent to about 10 percent by weight of a prostaglandin E compound, preferably $PGE_1$ (alprostadil), or a pharmaceutically acceptable salt thereof, about 0.025 to about 40 percent by weight of a $(C_1-C_4)$-alkyl $(C_8-C_{22})$ carboxylic ester (e.g., ethyl laurate), and about 0.025 percent to about 40 percent by weight of an N,N-di$(C_1-C_8)$ alkylamino substituted, $(C_4-C_{18})$ alkyl $(C_2-C_{18})$ carboxylic ester skin penetration enhancer (e.g., dodecyl 2-(N,N-dimethylamino)-propionate or a salt thereof).

Prostaglandin E (PGE) compounds have the 9-oxo, 11α-hydroxy substituents as well as unsaturation in the side chains. The compounds of this group include prostaglandin $E_1$ ($PGE_1$) represented by the formula

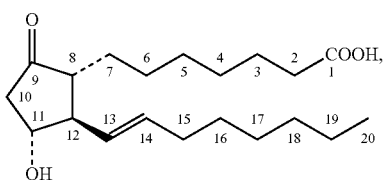 [SMILES: CCCCCC/C=C/[C@H]1[C@H](O)CC(=O)[C@@H]1CCCCCCC(=O)O]

prostaglandin $E_2$ (or $PGE_2$) represented by the formula

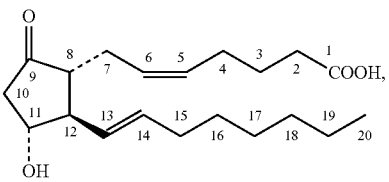 [SMILES: CCCCCC/C=C/[C@H]1[C@H](O)CC(=O)[C@@H]1C/C=C\CCCC(=O)O]

prostaglandin $E_3$ (or $PGE_3$) represented by the formula

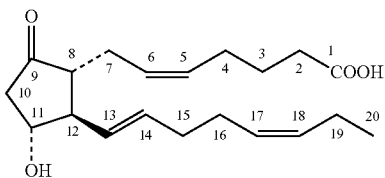 [SMILES: CC/C=C\CC/C=C/[C@H]1[C@H](O)CC(=O)[C@@H]1C/C=C\CCCC(=O)O]

as well as the pharmaceutically acceptable salts thereof.

PGE compounds have useful therapeutic activity as vasodilators and have been utilized to treat male and female sexual disorders, to control lipid metabolism, to treat ulcers, to treat inflammatory skin lesions, and the like therapeutic applications.

PGE compounds are relatively unstable, however, and tend to decompose, especially in aqueous solutions or in an aqueous environment. It has now been found however, that these compounds can be effectively stabilized in non-aqueous media that are substantially free from $C_1$-$C_4$ alcohols and include a ($C_1$-$C_4$)-alkyl ($C_8$-$C_{22}$) carboxylic ester, such as ethyl laurate. The PGE compositions of the invention can be combined with a suitable diluent (e.g., a buffered aqueous alcohol combination) to form a topical dosage form, such as a cream, gel, ointment, and the like, prior to use. Preferably, the ratio of thickening agent to ester is in the range of about 0.5:1 to about 1.5:1.

The PGE compositions can be provided as a semi-solid composition in a one part dosage form, or provided as a packaged, multi-part dosage form in which an actives compartment contains the PGE composition as a unit dose and a diluent compartment contains an aqueous alcohol diluent, which when combined with the PGE composition forms a unit dose for a topical application. In the packaged, multi-part dosage forms embodying the present invention, the actives compartment can also contain a non-aqueous liquid bulking agent, such as a silicone oil (e.g., a polydimethylsiloxane, such as cyclomethicone USP, dimethicone USP, and the like), a $C_6$-$C_{22}$ alcohol (e.g., benzyl alcohol or a fatty alcohol), and the like. The actives compartment, and optionally the diluent compartment, can include a thickening agent, such as a polysaccharide (e.g., a starch, a gum, a starch derivative, or a gum derivative), polyvinylpyrrolidone, polyvinyl alcohol, a cellulose derivative (e.g., hydroxymethyl cellulose, carboxymethyl cellulose, hydroxypropyl methylcellulose, and the like), a sugar (e.g., lactose), and the like.

The multi-part dosage form can comprise a two compartment pouch or packet having a frangible seal between the actives compartment and the diluent compartment, such that squeezing the pouch or packet can breach the seal and allow the contents of the two compartments to combine. The pouch can then be manually kneaded to thoroughly mix and emulsify the contents, affording a cream, ointment, or gel PGE topical dosage form. Alternatively, a clamp or the like can be used in lieu of a frangible seal.

$PGE_1$ and $PGE_2$ are well known to those skilled in the art. Reference may be had to various literature references for its pharmacological activities, side effects and normal dosage ranges. See for example, Physician's Desk Reference, 51st Ed. (1997), The Merck Index, 12th Ed., Merck & Co., N.J. (1996), and Martindale The Extra Pharmacopoeia, 28th Ed., London, The Pharmaceutical Press (1982). Prostaglandin $E_1$ as well as other PGE compounds referenced herein are intended to encompass also the pharmaceutically acceptable derivatives thereof, including physiologically compatible salts and ester derivatives.

Additionally, simultaneous administration of one or more non-ecosanoid vasodilators may be desirable and may in some cases exhibit a synergistic effect. The combination of prazosin with prostaglandin $E_1$ has been found to be particularly advantageous in this regard. Suitable non-ecosanoid vasodilators include, but are not limited to: nitrates such as nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine ("SNAP"); amino acids such as L-arginine; long and short acting α-adrenergic blockers such as phenoxybenzamine, dibenamine, phentolamine, tamsulosin and indoramin, especially quinazoline derivatives such as alfuzosin, bunazosin, doxazosin, terazosin, prazosin, and trimazosin; vasodilative natural herbal compositions and bioactive extracts thereof, such as gosyajinki-gan, *Satureja obovata*, bai-hua qian-hu, lipotab, saiboku-to, vinpocetine, *Gingko biloba*, bacopa, *Gynostemma pentaphyllum*, gypenosides, *Evodia rutaeacrpa*, rutaecarpine, dehydroevodiamine, dan-shen, salviae miltiorrhizae radix, shosaikoto, *Zizyphi fructus*, ginseng and mixtures thereof (U.S. Pat. No. 6,007,824); ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone and vasoactive intestinal peptides.

The quantity of a vasoactive prostaglandin, such as prostaglandin $E_1$, in the pharmaceutical composition is a therapeutically effective amount and necessarily varies according to the desired dose, the dosage form and the particular form of vasoactive prostaglandin used. The term "prostaglandin" as used generically herein refers to the prostaglandin free acid and pharmaceutically acceptable derivatives thereof, including, for example prostaglandin $E_1$ ($PGE_1$), pharmaceutically acceptable salts and lower alkyl esters thereof (the term "lower alkyl" as used herein means straight chain or branched chain alkyl containing one to four carbon atoms). The composition generally contains between 0.001 percent to 1 percent of vasoactive prostaglandin, e.g., prostaglandin $E_1$, typically contains between 0.05 percent to 1 percent, preferably from 0.1 percent to 0.5 percent, based on the total weight of the composition.

The prostaglandin E compositions of the invention preferably are utilized to provide packaged, multi-part dosage forms in which an actives compartment contains the prostaglandin E composition as a unit dose and a diluent compartment contains an aqueous alcohol diluent, which when combined with the prostaglandin E composition forms a unit dose for a topical application. In the packaged, multi-part dosage forms embodying the present invention, the actives compartment can also contain a non-aqueous liquid bulking agent, such as a silicone oil (e.g., a polydimethylsiloxane, such as cyclomethicone USP, dimethicone USP, and the like), a $C_6$-$C_{22}$ alcohol (e.g., benzyl alcohol or a fatty alcohol), and the like. The actives compartment, and optionally the diluent compartment, can include a thickening agent, such as a polysaccharide (e.g., a starch, a gum, a starch derivative, or a gum derivative), polyvinylpyrrolidone, polyvinyl alcohol, a cellulose derivative (e.g., hydroxymethyl cellulose, carboxymethyl cellulose, hydroxypropyl methylcellulose, and the like), a sugar (e.g., lactose), and the like.

The prostaglandin E compositions of the invention preferably are utilized to provide packaged, multi-part dosage forms in which an actives compartment contains the prostaglandin E composition as a unit dose and a diluent compartment contains an aqueous alcohol diluent, which when combined with the prostaglandin E composition forms a unit dose for a topical application. In the packaged, multi-part dosage forms embodying the present invention, the actives compartment can also contain a non-aqueous liquid bulking agent, such as a silicone oil (e.g., a polydimethylsiloxane, such as cyclomethicone USP, dimethicone USP, and the like), a $C_6$-$C_{22}$ alcohol (e.g., benzyl alcohol or a fatty alcohol), and the like. The actives compartment, and optionally the diluent compartment, can include a thickening agent, such as a polysaccharide (e.g., a starch, a gum, a starch derivative, or a gum derivative), polyvinylpyrrolidone, polyvinyl alcohol, a cellulose derivative (e.g., hydroxymethyl cellulose, carboxymethyl cellulose, hydroxypropyl methylcellulose, and the like), a sugar (e.g., lactose), and the like.

The prostaglandin E compositions of the invention include a skin penetration enhancer, which is an N,N-di($C_1$-$C_8$) alkylamino substituted, ($C_4$-$C_{18}$) alkyl ($C_2$-$C_{18}$) carboxylic esters or pharmaceutically acceptable acid addition salts thereof. As used herein, the term "($C_4$-$C_{18}$) alkyl ($C_2$-$C_{18}$) carboxylic ester" means an ester of a ($C_4$-$C_{18}$) alcohol and a ($C_2$-$C_{18}$) carboxylic acid. The term "N,N-di($C_1$-$C_8$) alkylamino substituted," in reference to a ($C_4$-$C_{18}$) alkyl ($C_2$-$C_{18}$) carboxylic ester means that either the alcohol portion or the carboxylic acid portion from which the ester is prepared bears an amino substituent $NR_xR_y$, wherein $R_x$ and $R_y$ are each independently a ($C_1$-$C_8$) alkyl group. Preferably $R_x$ and $R_y$ are both methyl groups.

Preferred N,N-di($C_1$-$C_8$) alkylamino substituted, ($C_4$-$C_{18}$) alkyl ($C_2$-$C_{18}$) carboxylic esters are dodecyl-2-(N,N-dimethylamino)-propionate (DDAIP); dodecyl-2-(N,N-dimethylamino)-acetate (DDAA); 1-(N,N-dimethylamino)-2-propyl dodecanoate (DAIPD); 1-(N,N-dimethylamino)-2-propyl myristate (DAIPM); 1-(N,N-dimethylamino)-2-propyl oleate (DAIPO); and pharmaceutically acceptable acid addition salts thereof. Particularly preferred is DDAIP, alone or in combination with an auxiliary permeation enhancer. DDAIP is available from Steroids, Ltd. (Chicago, Ill.). The preparation of DDAIP and crystalline acid addition salts thereof is described in U.S. Pat. No. 6,118,020 to Büyüktimkin, et al., which is incorporated herein by reference. Long chain similar amino substituted, alkyl carboxylic esters can be synthesized from readily available compounds as described in U.S. Pat. No. 4,980,378 to Wong, et al., which is incorporated herein by reference. Such amino-substituted carboxylic ester penetration enhancers are also sometimes referred to as alkyl-2-(N-substituted amino)-alkanoates and (N-substituted amino)-alkanol alkanoates. For convenient reference, alkyl-2-(N-substituted amino)-alkanoates and (N-substituted amino)-alkanol alkanoates can be grouped together under the term alkyl (N-substituted amino) esters.

The penetration enhancer is present in an amount sufficient to enhance the penetration of the prostaglandin E compound into tissue. The specific amount varies necessarily according to the desired release rate and specific form of prostaglandin E compound used. Generally, this amount is in the range of about 0.01 percent to about 20 percent, based on the total weight of a topical dosage is prepared by mixing a prostaglandin E composition of the invention and an aqueous alcoholic diluent, as described herein.

Natural and modified polysaccharides (e.g., gums) can be utilized as a viscosity enhancing agent for the prostaglandin E composition. Such thickening agent can optionally be present in the diluent or in both the prostaglandin E composition and the diluent. Suitable representative gums are the natural and modified galactomannan gums. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1->4). Single membered α-D-mannopyranosyl units, linked (1->6) with the main chain, are present as side branches. Galactomannan gums include guar gum, which is the pulverized endosperm of the seed of either of two leguminous plants (*Cyamposis tetragonalobus* and *psoraloids*) and locust bean gum, which is found in the endosperm of the seeds of the carob tree (*Ceratonia siliqua*). Suitable modified polysaccharide gums include ethers of natural or substituted polysaccharide gums, such as carboxylmethyl ethers, ethylene glycol ethers and propylene glycol ethers.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums: Polysaccharides & Their Derivatives*, Whistler R. L. and BeMiller J. N. (eds.), $3^{rd}$ Ed. Academic Press (1992) and Davidson R. L., *Handbook of Water-Soluble Gums and Resin*, McGraw-Hill, Inc., N.Y. (1980). Most gums are commercially available in various forms, commonly a powder, and ready for use in food and topical compositions. For example, locust bean gum in powdered form is available from Tic Gums Inc. (Belcam, Md.).

Thickening agents preferably are present in the range of about 0.025 to about 40 percent by weight in the prostaglandin E compositions of the invention, and about 0.1 percent to about 5 percent by weight, based on the total weight of a topical dosage form prepared by mixing a prostaglandin E composition and diluent. The preferred range of thickening agent present in the topical dosage form is about 0.5 percent to 3 percent.

Alternative thickening agents include cross-linked polyacrylic acid polymers and cellulose derivatives (e.g., carboxymethyl cellulose, hydroxymethyl cellulose, hydroxypropyl methyl cellulose, and the like).

A common variety of polyacrylic acid polymer is known generically as "carbomer." Carbomer is polyacrylic acid polymers lightly cross-linked with polyalkenyl polyether. It is commercially available from the B. F. Goodrich Company (Akron, Ohio) under the designation "CARBOPOL®." A particularly preferred variety of carbomer is that designated as "CARBOPOL® 940."

Other polyacrylic acid polymers suitable for use are those commercially available under the designation "PEMULEN™" (B.F. Goodrich Company) and "POLYCARBOPHIL™" (A. H. Robbins, Richmond, Va.). The PEMULEN™ polymers are copolymers of $C_{10}$ to $C_{30}$ alkyl acrylates and one or more monomers of acrylic acid, methacrylic acid or one of their simple esters cross-linked with an allyl ether of sucrose or an allyl ether of pentaerythritol. The POLYCARBOPHIL™ product is polyacrylic acid cross-linked with divinyl glycol. Where polyacrylic acid polymers are present, they represent about 0.5 percent to about 5 percent of the composition, based on its total weight.

The concentration of $(C_1-C_4)$-alkyl $(C_8-C_{22})$ carboxylic ester (e.g., ethyl laurate, isopropyl myristate, isopropyl laurate, or a mixture of two or more thereof) in the prostaglandin E compositions of the invention necessarily varies according to various factors such as the desired semi-solid consistency and the desired skin penetration promoting effects. Suitably, the concentration of $(C_1-C_4)$-alkyl $(C_8-C_{22})$ carboxylic ester is the range of about 0.025 percent to about 40 percent by weight based on the total weight of the prostaglandin E composition. The preferred composition contains a $(C_1-C_4)$-alkyl $(C_8-C_{22})$ carboxylic ester in the range of about 0.5 percent to about 35 percent by weight based on the total weight of the prostaglandin E composition.

An optional, but preferred, component is an emulsifier, which can be present in the prostaglandin E composition or in the diluent. A suitable emulsifier generally exhibits a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate, present in an amount up to about 2 percent, based on the total weight of the composition, is preferred. The preferred amount of sucrose stearate emulsifier can also be expressed as a weight ratio of emulsifier to polysaccharide gum.

Other suitable emulsifiers are the polyoxyethylene sorbitan esters, long chain alcohols, preferably cetostearyl alcohol, and fatty acid glycerides. Suitable polyoxyethylene sorbitan esters include the monolaurate (TWEEN® 20, SPAN® 20) the monopalmitate (TWEEN® 40), the monostearate (TWEEN® 60), and the monooleate (TWEEN® 80) and mixtures thereof. Preferred fatty acid glycerides include glyceryl monooleate, triolein, trimyristin and tristearin.

Another optional ingredient is an antifoam agent, a chemical that reduces the tendency of the finished preparation to generate foam on shaking or agitation. Silicones are the preferred antifoam agents; however, a wide variety of alcohols and lipids exhibit similar properties. With the exception of alcohols, the selected antifoam agent must be effective in relatively small concentrations, and are employed in trace amounts. Illustrative antifoam agents are dimethicone, cetyl dimethicone, dimethicone silylate, dimethiconol, a mixture of dimethicone and hydrated silica, isopropyl alcohol, hexyl alcohol, trimethylsiloxysilicate, triphenyl trimethicone and the like. A particularly preferred antifoam agent is a mixture of dimethicone with an average chain length of 200 to 300 dimethylsiloxane units and hydrated silica, commercially available under the designation SIMETHICONE® USP from Dow Corning Corporation, Michigan.

The prostaglandin E compositions of the invention are substantially free from $C_1-C_4$ alcohols (e.g., methanol, ethanol, and the like). It has been found that lower alkyl alcohols, such as ethanol, can lead to degradation of prostaglandin E compounds during storage for prolonged periods of time (e.g., weeks to months). As used herein, the phrase "substantially free from $C_1-C_4$ alcohols" means that the compositions do not contain a destabilizing amount of lower alkyl alcohols. Preferably, the compositions contain not more than trace levels of lower alkyl alcohols, which may be present as a byproduct or contaminant from one or more of the components of the prostaglandin E composition (e.g., trace ethanol from ethyl laurate). Typically, the prostaglandin E compositions of the invention include not more than about 0.5 percent by weight of $C_1-C_4$ alcohols prior to mixing with a diluent.

Aqueous alcoholic diluents useful for mixing with the prostaglandin E compositions of the invention can include one or more buffering agents (i.e., buffer systems), if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents, which are thus responsible for a resistance or change in pH from a starting buffered pH value in the range indicated above are well known. While there are countless suitable buffers, potassium phosphate buffers (e.g., potassium phosphate monohydrate, $KH_2PO_4$ N.F., and the like) have proven effective for compositions of the present invention and are preferred.

The final pH value of the topical composition prepared by the combination of prostaglandin E composition and diluent may vary within the physiological compatible range. Necessarily, the final pH value is one not irritating to human skin and preferably such that transdermal transport of the prostaglandin E compound is facilitated. Without violating this constraint, the pH may be selected to improve prostaglandin E compound stability and to adjust consistency when required. In one embodiment, the preferred pH value is about 3.0 to about 7.4, more preferably about 3.0 to about 6.5, most preferably from about 3.5 to about 6.0.

Preferably, the water present in the diluent is purified, e.g., deionized water. The diluent preferably contains water in the range of more than about 5 to about 95 percent by weight based on the total weight of the diluent. The specific amount of water present is not critical, however, being adjustable to obtain the desired viscosity (usually about 50 cps to about 30,000 cps) and/or concentration of the combination when mixed with the prostaglandin E composition. The topical composition formed by mixing the prostaglandin E composition and diluent preferably has a viscosity of at least about 30 centipoise. Viscosity enhancing agents can be included to afford the desired level of viscosity. The diluent also preferably includes up to about 95 percent by weight of a $C_1$-$C_4$ alcohol (e.g., ethanol).

Prostaglandin E compound stabilizers and excipients, such as organic acids and alcohols, cyclodextrins, coloring agents, rheological agents, and preservatives can be added to the extent that they do not limit the stability or penetration of the prostaglandin E compound.

The ingredients listed above may be combined in any order and manner that produces a composition for ultimately receiving the prostaglandin E compound, such as prostaglandin $E_1$ and the like, preferably substantially evenly dispersed throughout. Methods of mixing and compounding pharmaceutical compositions, such as the prostaglandin E compositions of the invention, are well known in the art.

A preferred diluent for use in a two-part packaged dosage form of the invention comprises 1 to about 20 percent by weight ethanol, 80 to 99 percent by weight water, and a suitable amount of one or more buffering agent to maintain a desired physiologically compatible pH in a topical dosage form prepared by combining the prostaglandin E composition and diluent.

Variations in the treating compositions which do not adversely affect the effectiveness of the prostaglandin E compound would be evident to one skilled in the art, and are within the scope of this invention. For example, additional ingredients such as coloring agents, anti-microbial preservatives, emulsifiers, lubricants, perfumes, prostaglandin E compound stabilizers, and the like, may be included as long as the resulting preparation retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). A fragrance can be included in the composition in an amount up to about 5 percent by weight, based on the total weight of the composition. Suitable perfumes and fragrances are known in the art. A non-limiting example of a suitable fragrance is myrtenol, preferably utilized in an amount of up to about 2 percent by weight.

The compositions of the present invention can also include a small amount (e.g., about 0.01 to about 4 percent by weight) of a topical anesthetic, if desired. Typical topical anesthetics include lidocaine, benzocaine, dyclonine, dibucaine, pharmaceutically acceptable salts and mixtures thereof. In one preferred embodiment, the topical anesthetic is about 0.5 percent dyclonine, based on the weight of the composition.

An illustrative two-component dosage form is set forth in Table 1, below:

TABLE 1

| | Amount, parts by weight | |
|---|---|---|
| | Preferred | More Preferred |
| Actives compartment | | |
| A prostaglandin E compound such as $PGE_1$ | 0.025-10 | 0.5-5 |
| A skin penetration enhancer (e.g., dodecyl 2-(N,N-dimethylamino)-propionate•HCl) | 0.025-40 | 0.4-35 |
| A ($C_1$-$C_4$)-alkyl ($C_8$-$C_{22}$) carboxylic ester (e.g., ethyl laurate) | 0.025-40 | 0.5-35 |

TABLE 1-continued

| | Amount, parts by weight | |
|---|---|---|
| | Preferred | More Preferred |
| A viscosity enhancer (e.g., guar gum) | 0.025-40 | 0.5-35 |
| Diluent compartment | | |
| Water (deionized or U.S.P.) | 5-95 | 40-95 |
| Ethanol | 1-75 | 3-40 |
| Phosphate buffer (pH 5.5) | Q.S. | |

If desired, preservatives such as methyl paraben, propyl paraben, benzalkonium chloride, benzethonium chloride, and the like, can be included in the PGE composition and/or the diluent, as well. The prostaglandin E composition and diluent can be combined with agitation to form a topical prostaglandin E dosage form.

In another embodiment, compounds of prostaglandin E group are stabilized as non-aqueous compositions that include the compound together with a bulking agent that can be a non-aqueous liquid, or a solid in sheet, film, or powder form. Optionally, a skin penetration enhancer can be present. Suitable such compositions are disclosed in U.S. Pat. No. 6,841,574, which is incorporated herein by reference. Such a preferred non-aqueous, solid dosage form comprises a compound of prostaglandin E group substantially uniformly distributed in a carrier sheet or film. A predetermined size portion of this sheet or film can be applied to the surface of a moistened body part or introduced directly into a moist body cavity to release the prostaglandin compound. Alternatively a predetermined size portion of the sheet or film that includes a prostaglandin compound can be dissolved in an aqueous or non-aqueous solvent that serves as a physiologically compatible delivery vehicle for the prostaglandin compound. For topical applications, the topical delivery vehicle is viscous and substantially non-flowing, such as a cream, gel, or ointment.

Prostaglandin E compounds can be incorporated as substantially uniformly distributed solids in a sheet-form material, i.e., sheet or film, of a physiologically compatible polymeric material, e.g., a cellulosic ether such as hydroxypropyl cellulose, hydroxypropyl methyl cellulose, and the like, a polysaccharide such as starch, polyvinylpyrrolidone, and the like. Sheet-form materials having a thickness of no more than about 10 mils are commonly referred to as films, and those having a thickness of more than about 10 mils are commonly referred to as sheets. The term "sheet-form" as used herein and in the appended claims refers to sheets as well as films. The sheet-form material can be a solid or a porous material, e.g., a sponge or the like. The sheet-form material containing a prostaglandin E compound dispersed therein can be converted into discs, tablets, pellets, and the like, if desired.

These sheet-form articles of manufacture can be water soluble for direct introduction into moist body cavities or soluble in a non-aqueous physiologically compatible solvent for the preparation of a cream or ointment suitable for topical application. The water soluble moiety of the prostaglandin-bearing sheet-form material can also be utilized, of course, for the preparation of aqueous gels based on a polycarbophil, a polyoxyethylene-polyoxypropylene block copolymer, e.g., the so-called poloxamers, and on mixtures thereof, as well as non-aqueous gels based on the polysorbates, liquid block copolymers of propylene oxide and ethylene oxide, and the like.

If desired, the prostaglandin E compound-bearing sheet form materials of the present invention can also include physiologically compatible plasticizers, solubility enhancers (e.g., hydroxypropyl-beta-cyclodextrin), and the like.

These prostaglandin E-bearing sheet-form materials can be prepared by first forming a solution of the desired prostaglandin E compound in a non-aqueous solvent such as a $C_2$ to $C_4$ aliphatic alcohol, e.g., methanol, ethanol, propanol, isopropanol, n-butanol and the like, together with the polymeric material, with or without a skin penetration enhancer, then casting the solution continuously on a roll or batchwise in a shallow dish or pan, and thereafter evaporating the solvent therefrom. The resulting sheet or film has the prostaglandin E compound substantially uniformly distributed throughout in an non-aqueous medium that can be readily subdivided and apportioned into desired unit doses each having a predetermined PGE content. The cast sheet or film can also be retained on a solid surface for storage and dissolved immediately prior to use.

In other embodiments, the prostaglandin E compound is incorporated in a transdermal patch. Suitable transdermal patches are disclosed, for example in U.S. Pat. Nos. 5,480,648 and 7,087,240.

The foregoing unit doses can be utilized to provide packaged, paired compartment dosage forms in which an actives compartment contains the prostaglandin E compound unit dose and an inerts compartment contains the delivery vehicle for a topical application. In the packaged, paired-compartment dosage forms embodying the present invention, the actives compartment can also contain the prostaglandin E compound together with a bulking agent in a non-aqueous liquid, particulate or granular form. Suitable liquid bulking agents are silicone oils such as the polydimethylsiloxanes, e.g., cyclomethicone USP, dimethicone USP, and the like. Suitable solid bulking agents for this particular purpose are the cyclodextrins such as hydroxypropyl-beta-cyclodextrin, beta cyclodextrin, gamma cyclodextrin, and the like, the polysaccharides such as starches, gums, and the like polyvinylpyrrolidone, polyvinyl alcohol, the methyl celluloses, sugars, and the like.

A particularly preferred present solid dosage form comprises at least one PGE compound, preferably $PGE_1$, and an alkyl (N-substituted amino) ester, both substantially uniformly distributed in the carrier sheet or admixed with one another in an actives compartment of a packaged paired-compartment dosage form. $PGE_1$ and $PGE_2$ are particularly preferred vasoactive agents for the present purposes.

Among the suitable penetration enhancers for use in the present solid dosage forms dodecyl 2-(N,N-dimethylamino)-propionate and crystalline salts thereof are generally preferred. The preparation of such crystalline salts is described in U.S. Pat. No. 6,118,020 to Büyüktimkin et al.

The penetration enhancer is present in an amount sufficient to enhance the penetration of the prostaglandin E compound into tissue. The specific amount varies necessarily according to the desired release rate and specific form of prostaglandin E compound used. Generally, this amount is in the range of about 0.01 percent to about 20 percent, based on the total weight of the composition.

The desired release rate, including controlled or sustained release of the active compound can also be modulated by selection of the topical delivery vehicle, e.g., a hydrophobic vehicle such as polydimethylsiloxanes and the like. Carboxy-terminated polydimethylsiloxanes can also enhance skin permeation by the active compound.

Natural and modified polysaccharide gums can also be present as part of the carrier sheet or the topical delivery vehicle. Suitable representative gums are the natural and modified galactomannan gums, as described above. Suitable modified polysaccharide gums include ethers of natural or substituted polysaccharide gums, such as carboxylmethyl ethers, ethylene glycol ethers and propylene glycol ethers.

When present, the polysaccharide gums are present in the range of about 0.1 percent to about 5 percent, based on the total weight of the composition, with the preferred range being in the range of about 0.5 percent to 3 percent. In one preferred embodiment, about 2.5 percent by weight of a polysaccharide gum is present. An optional alternative to the polysaccharide gum is a polyacrylic acid polymer, as described above.

The concentration of lipophilic compound required necessarily varies according to other factors such as the desired semi-solid consistency and the desired skin penetration promoting effects. Suitably the concentration of lipophilic compound is the range of about 0.5 percent to about 40 percent by weight based on the total weight of the composition. The preferred topical composition contains lipophilic compound in the range of about 7 percent to about 40 percent by weight based on the total weight of the composition.

Where a mixture of aliphatic alcohol and aliphatic ester are employed, the suitable amount of alcohol is in the range of about 0.5 percent to about 75 percent. In one preferred embodiment, the amount of alcohol is in the range of about 5 percent to about 15 percent, while that of aliphatic ester is in the range of about 2 percent to about 15 percent (again based on the total weight of the composition). In another preferred embodiment, the amount of alcohol is in the range of about 0.5 percent to about 10 percent, while that of aliphatic ester is in the range from zero percent to about 10 percent (again based on the total weight of the composition).

An optional, but preferred, component is an emulsifier. A suitable emulsifier generally exhibits a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate, present in an amount up to about 2 percent, based on the total weight of the composition, is preferred. The preferred amount of sucrose stearate emulsifier can also be expressed as a weight ratio of emulsifier to polysaccharide gum.

Other suitable emulsifiers are the polyoxyethylene sorbitan esters, long chain alcohols, preferably cetostearyl alcohol, and fatty acid glycerides. Suitable polyoxyethylene sorbitan esters include the monolaurate (TWEEN® 20, Span 20) the monopalmitate (TWEEN® 40), the monostearate (TWEEN® 60), and the monooleate (TWEEN® 80) and mixtures thereof. Preferred fatty acid glycerides include glyceryl monooleate, triolein, trimyristin and tristearin. Another optional ingredient is an antifoam agent, a chemical that reduces the tendency of the finished preparation to generate foam on shaking or agitation.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate has proven effective for compositions of the present invention and is preferred.

The final pH value of the pharmaceutical composition may vary within the physiological compatible range. Necessarily, the final pH value is one not irritating to human skin and preferably such that transdermal transport of the prostaglandin E compound is facilitated. Without violating this constraint, the pH may be selected to improve prostaglandin E compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Prostaglandin E compound stabilizers such as organic acids and alcohols, cyclodextrins, coloring agents, rheological agents, and preservatives can be added to the extent that they do not limit penetration of the prostaglandin E compound.

The ingredients listed above may be combined in any order and manner that produces a composition for ultimately receiving the prostaglandin E compound, such as $PGE_1$ and the like, preferably substantially evenly dispersed throughout. One available approach to preparing such compositions involves evenly dispersing the polysaccharide gum (or polyacrylic acid) in a premixed water/buffer solution and then thoroughly homogenizing (i.e., mixing) the resulting mixture. When present, the emulsifier is added to the water/buffer solution before dispersing the polysaccharide gum. Any suitable method of adjusting pH value to the desired level may be used, for example, by adding concentrated phosphoric acid or sodium hydroxide.

The prostaglandin E compound, with or without a penetration enhancer, is then combined therewith prior to use with mixing.

In one embodiment, a preparation ready for application comprises about 0.01 percent to about 5 percent modified polysaccharide gum; about 0.001 percent to about 1 percent of a prostaglandin E compound, preferably $PGE_1$, or a pharmaceutically acceptable salt thereof; a lower alkyl ester thereof and mixtures thereof; about 0.5 percent to about 10 percent dodecyl 2-(N,N-dimethylamino)-propionate or a salt thereof; about 0.5 percent to about 10 percent of a lower alcohol selected from the group consisting of ethanol, propanol, isopropanol and mixtures thereof; about 0.5 percent to about 10 percent on an ester selected from the group consisting of ethyl laurate, isopropyl myristate, isopropyl laurate and mixture thereof; based on the weight of the preparation, together with an acid buffer. Preferably the preparation also comprises up to about 2 percent by weight sucrose stearate.

Variations in the treating compositions which do not adversely affect the effectiveness of the prostaglandin E compound would be evident to one skilled in the art, and are within the scope of this invention. For example, additional ingredients such as coloring agents, anti-microbial preservatives, emulsifiers, lubricants, perfumes, prostaglandin E compound stabilizers, and the like, may be included as long as the resulting preparation retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). Suitable perfumes and fragrances are known in the art; a suitable fragrance is up to about 5 percent and fragrances are known in the art; a suitable fragrance is up to about 5 percent myrtenol, preferably about 2 percent myrtenol, based on the total weight of the composition. The compositions of the present invention can also include a small amount, about 0.01 to about 4 percent by weight, of a topical anesthetic, if desired. Typical topical anesthetics include lidocaine, benzocaine, dyclonine, dibucaine, pharmaceutically acceptable salts and mixtures thereof. In one preferred embodiment, the topical anesthetic is about 0.5 percent dyclonine, based on the weight of the composition.

EXAMPLE 1

A placebo controlled study was performed in an animal model of Raynaud's disease to examine the effect of application of a topical prostaglandin $E_1$ composition in response to a 16° C. cold challenge. The results showed that topical application of a composition containing 0.22 weight percent prostaglandin $E_1$ produced a substantial increase in blood flow.

TABLE 2

| Ingredient | Weight percent | |
|---|---|---|
| | Test | Placebo |
| alprostadil, USP | 0.22 | — |
| Guar gum (Jaguar HP-120, Rhodia) | 2.5 | 2.5 |
| DDAIP HCl | 2.5 | 2.5 |
| Ethanol, anhydrous | 5.0 | 5.0 |
| Ethyl laurate, FCC, Penta | 3.0 | 3.0 |
| Potassium phosphate, monobasic | qs pH | qs pH |
| Phosphoric acid | qs pH | qs pH |
| Sodium hydroxide | qs pH | qs pH |
| Purified water | qs | qs |

Female hairless rats (about 250 g, Harlan Laboratories, Inc., Indianapolis, Ind.) were used for the test and placebo groups (ten rats per group). The test and placebo compositions having the ingredients list in Table 2, above, were prepared and stored at 4° C. The rats were placed in restraint, and test composition or placebo composition that had been allowed to come to room temperature was applied to the entire tail of each rat 10 minutes before the cold challenge, the test group receiving the test composition at a dose of 220 µg of alprostadil, and the control group receiving the placebo composition. The cold challenge was performed by submerging the tails into a 16° C. cold water bath.

Blood flow and temperature of the skin at the base of the tail were measured using a laser Doppler flowmeter and an infrared thermometer at the following times: before application of the cream (t minus 10 minutes), 10 minutes after the application of the cream (immediately before the start of the cold challenge at $t_0$), and at 30, 60, and 90 minutes after the start of the 16° C. (60.8° F.) cold challenge. When making the measurements, the tail was removed from the water bath and wiped dry before the blood flow and temperature were measured. The tails were replaced in the water bath immediately after the measurements were made.

Figure 2:
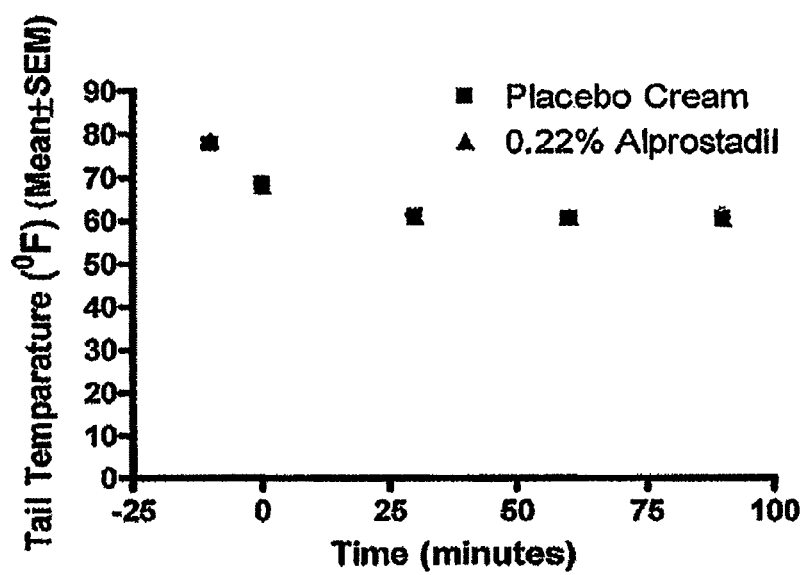
FIG. 2 is a graphical representation of the results of a study of the effects of a topical prostaglandin composition on peripheral temperature in response to a 16° C. cold challenge in an animal model.

The results of the study are presented in FIG. 1 and FIG. 2. FIG. 1 is a graphical representation of the results of a study of the effects of a topical prostaglandin composition on peripheral blood flow in response to a 16° C. cold challenge. The mean tail blood flow (as Electric Flux=V*m) and the standard error of the mean are plotted against time for treatment with the test alprostadil composition (filed triangles) and the placebo composition (filled squares). A significant increase in blood flow is seen in the alprostadil treated group that peaks at 60 minutes. FIG. 2 is a graphical representation of the results of a study of the effects of a topical prostaglandin composition on peripheral temperature in response to a 16° C. (60.8° F.) cold challenge. Both test and placebo groups showed a similar reduction in tail temperature that approached that of the water bath when the animals treated with the alprostadil composition produced a substantial increase in blood flow compared to the control group (compare FIG. 1 and FIG. 2 at 30, 60 and 90 minutes).

EXAMPLE 2

A randomized, placebo (vehicle) controlled, double blind cross-over designed dose ranging study trial is performed to assess the efficacy and tolerability of alprostadil alprostadil for Raynaud's phenomenon secondary to systemic sclerosis the ability of a test compound to increase blood flow in the fingers of study subjects Objectives:

The primary objective is to decrease a Composite Index for Raynaud's Phenomenon (including Raynaud's Condition Score (RCS), patient global assessment, physician global assessment, attack frequency, attack duration and attack Symptom Score (pain, numbness and tingling) in patients with Raynaud's phenomenon secondary to systemic sclerosis following treatment with topical alprostadil across a range of doses for 4 week in-life period and to determine the optimal dose for clinical usage.

Secondary objectives include assessments of tolerability as well as other clinical measures of quality of life and subject functional status as well as pilot information regarding clinical effects on healing and prevention of digital tip ischemic ulceration.

Substudies include assay of 15-keto-PG after both acute and chronic dosing (pharmacokinetics) as well as laser Doppler velocimetry studies of digital perfusion during cold challenge to clarify physiologic effects (pharmacodynamics).

Study Design:

This is a phase 3 multicenter, prospective, randomized, double-blind, within-cohort crossover design study of topical alprostadil in subjects with Raynaud's Phenomenon secondary to systemic sclerosis. The subjects, Principal Investigator (PI), clinical staff and medical monitor remain blinded to study drug administration. Eligible subjects who provide informed consent are randomized to one of three treatment groups:

Group 1: Placebo run-in; alprostadil topical cream, 0.33% w/w in 50 mg of cream (165 µg alprostadil) or placebo applied to each hand three times daily; wash-out; placebo or alprostadil topical cream, 0.33% w/w in 50 mg of cream (165 µg alprostadil) applied to each hand three times daily, resulting in a total dose of 990 µg alprostadil applied daily.

Group 2: Placebo run-in; alprostadil topical cream, 0.42% w/w in 112.5 mg of cream (472.5 µg alprostadil) or placebo applied to each hand three times daily; wash-out; placebo or alprostadil topical cream, 0.42% w/w in 112.5 mg of cream (472.5 µg alprostadil) applied to each hand three times daily, resulting in a total dose of 2835 µg alprostadil applied daily Group 3: Placebo run-in; alprostadil topical cream, 0.42% w/w in 225 mg of cream (945 µg alprostadil) or placebo applied to each hand three times daily; wash-out; placebo or alprostadil topical cream, 0.42% w/w in 225 mg of cream (945 µg alprostadil) applied to each hand three times daily, resulting in a total dose of 5670 µg alprostadil applied daily The order of treatments, placebo vs active study drug, is randomized.

Subjects are observed for one week prior to receiving placebo (vehicle cream). After two weeks of self-administration of topical placebo cream (vehicle), subjects self-administer topical active study drug or placebo at their assigned dose. After four weeks of active treatment, subjects have a two week wash-out period. Following the wash-out period, subjects cross-over to the other treatment (placebo or assigned dose of active study drug) for four weeks. Subjects then cease therapy and are followed for two weeks (refer to Table 3). The Schedule of Assessments is presented in Table 4, below.

TABLE 3

Study Design

LEAD-IN CYCLE (all subjects)

| Day −21* | Day −20 | Day −19 | Day −18 | Day −17 | Day −16 | Day −15 |
|---|---|---|---|---|---|---|
| No Treatment | No Treatment | No Treatment | No Treatment | No Treatment | No Treatment | No Treatment |
| Day −14* | Day −13 | Day −12 | Day −11 | Day −10 | Day −9 | Day −8 |
| Placebo | Placebo | Placebo | Placebo | Placebo | Placebo | Placebo |
| Day −7 | Day −6 | Day −5 | Day −4 | Day −3 | Day −2 | Day −1 |
| Placebo | Placebo | Placebo | Placebo | Placebo | Placebo | Placebo |

TABLE 3-continued

Study Design

*Clinic visit

Placebo-responders ⇒ withdrawn from study

Placebo non-responders ⇓ randomized to one of three dose levels:

| TREATMENT CYCLE 1 | | |
|---|---|---|
| Group 1<br>Days 1 to 28[1] | Group 2<br>Days 1 to 28[1] | Group 3<br>Days 1 to 28[1] |
| Active or placebo | Active or placebo | Active or placebo |

[1]The last day of each cycle is a clinic visit
Group 1: Placebo run-in; alprostadil topical cream, 0.33% w/w in 50 mg of cream (165 μg alprostadil) or placebo applied to each hand three times daily; wash-out; placebo or alprostadil topical cream, 0.33% w/w in 50 mg of cream (165 μg alprostadil) applied to each hand three times daily, resulting in a total dose of 990 μg alprostadil applied daily.
Group 2: Placebo run-in; alprostadil topical cream, 0.42% w/w in 112.5 mg of cream (472.5 μg alprostadil) or placebo applied to each hand three times daily; wash-out; placebo or alprostadil topical cream, 0.42% w/w in 112.5 mg of cream (472.5 μg alprostadil) applied to each hand three times daily, resulting in a total dose of 2835 μg alprostadil applied daily
Group 3: Placebo run-in; alprostadil topical cream, 0.42% w/w in 225 mg of cream (945 μg alprostadil) or placebo applied to each hand three times daily; wash-out; placebo or alprostadil topical cream, 0.42% w/w in 225 mg of cream (945 μg alprostadil) applied to each hand three times daily, resulting in a total dose of 5670 μg alprostadil applied daily.

| WASHOUT CYCLE | | |
|---|---|---|
| Group 1<br>Days 29 to 42[1] | Group 2<br>Days 29 to 42[1] | Group 3<br>Days 29 to 42[1] |
| No Study Drug | No Study Drug | No Study Drug |

[1]The last day of each cycle is a clinic visit
[1]The last day of each cycle is a clinic visit
Treatment Crossover

| TREATMENT CYCLE 2 | | |
|---|---|---|
| Group 1<br>Days 43 to 70[1] | Group 2<br>Days 43 to 70[1] | Group 3<br>Days 43 to 70[1] |
| Active or placebo | Active or placebo | Active or placebo |

[1]The last day of each cycle is a clinic visit
Group 1: Placebo run-in; alprostadil topical cream, 0.33% w/w in 50 mg of cream (165 μg alprostadil) or placebo applied to each hand three times daily; wash-out; placebo or alprostadil topical cream, 0.33% w/w in 50 mg of cream (165 μg alprostadil) applied to each hand three times daily, resulting in a total dose of 990 μg alprostadil applied daily.
Group 2: Placebo run-in; alprostadil topical cream, 0.42% w/w in 112.5 mg of cream (472.5 μg alprostadil) or placebo applied to each hand three times daily; wash-out; placebo or alprostadil topical cream, 0.42% w/w in 112.5 mg of cream (472.5 μg alprostadil) applied to each hand three times daily, resulting in a total dose of 2835 μg alprostadil applied daily
Group 3: Placebo run-in; alprostadil topical cream, 0.42% w/w in 225 mg of cream (945 μg alprostadil) or placebo applied to each hand three times daily; wash-out; placebo or alprostadil topical cream, 0.42% w/w in 225 mg of cream (945 μg alprostadil) applied to each hand three times daily, resulting in a total dose of 5670 μg alprostadil applied daily.

| LEAD-OUT CYCLE | | |
|---|---|---|
| Group 1<br>Days 71 to 84[1] | Group 2<br>Days 71 to 84[1] | Group 3<br>Days 71 to 84[1] |
| No Study Drug | No Study Drug | No Study Drug |

Subjects are evaluated in the clinic prior to receiving the next study drug regimen. If subjects tolerate the treatment regimen, subjects proceed to the next phase of therapy. Safety is assessed by recording the occurrence of adverse events (AEs), as well as by changes in vital signs, laboratory data and physical examinations.

TABLE 4

Schedule of Assessments and Procedures

| Protocol Activity | Screen Day −21 | ReScreen Day −14 | Day 0 | Day 28 | Day 42 | Day 70 | Day 84 |
|---|---|---|---|---|---|---|---|
| Informed Consent | X | | | | | | |
| Hx Physical Exam | X | | | X | | X | X |
| Weight and Vital Signs | X | | | X | | X | |
| Laboratory CBC, chemistries, U/A | X | | | X | | X | |
| Urine Pregnancy | X | | | | | | |
| Diary Instruction | X | X | | | | | |
| Diary Review | | X | X* | X | X | X | |
| Placebo | | X | | | X | | |
| Investigational Treatment | | | X | | | | |
| Concomitant Med | X | X | X | X | X | X | |
| SHAQ | X | | | X | | X | |
| SF-36 | X | | | X | | X | |
| Adverse Events | X | X | X | X | X | X | X |
| 15-keto-PG assay+ | | | X | | X | | |
| Laser Doppler Cold Challenge++ | | | X | X | X | X | |

*Diary review - exclude >20% improvement in Diary
+Time 0, 1, 6 hour (in selected centers)
++In selected centers Study Compositions:
1) alprostadil topical cream, 0.33% w/w in 100 mg of cream (330 µg alprostadil).
2) alprostadil topical cream, 0.42% w/w in 225 mg of cream (945 µg alprostadil).
3) Matching Placebo Cream applied as a single application to both hands three times daily.

Inclusion Criteria:
1. Males or females 18 to 70 years of age.
2. Active Raynaud's Phenomenon defined as episodic digital pallor with/or without following cyanosis and/or erythema in response to environmental cold or emotional stress.
3. Diagnosis of systemic sclerosis by fulfilling the preliminary Classification Criteria of the American College of Rheumatology.
4. At least seven episodes of Raynaud's Phenomenon per week during one week of patient diary.
5. Clinically stable disease and stable use of other Raynaud's therapies including calcium channel blockers and Type V phosphodiesterase inhibitors over the previous two months.
6. Stable immunosuppressant treatment over 3 months.
7. Willing and able to provide written informed consent; where permitted, a subject's legally authorized representative may provide written informed consent.
8. Negative pregnancy test within 1 week prior to dosing in women of childbearing potential (defined as not amenorrheic for >2 years or not surgically sterilized).
9. Willing and able to comply with all study procedures and restrictions.
10. Adequate hand function to be able to self-administer the study composition.

Exclusion Criteria:
1. Current smoker or use of nicotine products. Former smokers must have stopped >6 months prior to study entry.
2. History of stroke, myocardial infarction, life-threatening arrhythmia, uncontrolled hypertension, systemic blood pressure <100/60, uncontrolled diabetes mellitus or unstable angina.
3. Hepatic cirrhosis, active hepatitis, acute or chronic renal insufficiency.
4. History of upper extremity surgical sympathectomy within the previous six months.
5. Active alcoholism or drug abuse within the previous 5 years.
6. Pregnant or breast feeding or considering pregnancy in the next 4 months
7. Past or present major psychiatric illness.
8. Participation in another investigational drug study within the previous 30 days.
9. Use of any oral, inhaled or parenteral prostacyclins within the previous 6 months.

Subjects excluded for any of the reasons listed above may be re-screened for participation at any time following consultation with the PI and Sponsor if the exclusion criteria have changed.

Outcome measures include laser Doppler imaging (LDI) of the dorsum of hands and fingers for both placebo and test composition-treated hands. The same wavelength, scanning speed, scanning distance, DC values, and image normalization is used for all patients. Measurements are made from discrete regions of a finger and hand or average measurements of entire digit(s). LDI data collected from discrete outlined areas on the dorsum of the finger and dorsum of hand are averaged, or a ratio between distal vs. proximal flow is calculated. Where average measurements of digit(s) are performed the mean cutaneous flow in the entire finger from the base of the phalanx, up to and including the nailbed, is used. LDI is performed at several time points. Baseline measurements are taken after equilibration in room temperature, 10 minutes later, just prior to the application of the test composition, immediately after application of test composition, 5 minutes and 10 minutes after application of the test composition; the 10 minute measurement point is immediately prior to the cold challenge, immediately after the cold challenge, and at several time points (5', 10', 15', 20', 30', 1 hour, 3 hour, 6 hour) after the cold challenge.

Infrared computerized thermography is done on the both the dorsal and volar surface of both hands immediately following LDI, taking measurements at the same time points listed. Proximal-distal differences are noted. Prior studies have detected differences between the dorsum of the fingertips versus the dorsum of the hand in patients with Raynaud's disease.

Patient reports are also recorded at the time points listed above, including a visual analogue scale (VAS) pain report and sensations such as numbness, tingling, burning, cold, pain, greasiness. When the above patient reports are taken, the patient's heart rate and blood pressure are also recorded.

LDI and thermography measurements are compared between the test composition and placebo treated fingers.

Depending upon the patient's response, it may be better to compare the corresponding fingers individually rather than averaging the measurements for all the fingers on one hand compared to the average measurements of all the fingers on the other hand. The vasospasm of Raynaud's disease can selectively occur in a subset of fingers or parts of the finger. If measurements are made of the distal and proximal portion of the hand, then the ratio of these values can be compared. Areas that respond to treatment should have a ratio closer to 1, while in the typical Raynaud's disease attack, the ratio would be <1. Baseline temperature changes of 2° C. or greater have been found to be significant in other studies.

The test composition and placebo composition are provided in identical packages except for identifying numbers. Two examiners/technicians who are blinded as to package content simultaneously apply one of the study compositions to each hand. The study compositions are applied to the entire hand, including the web spaces, with a room temperature applicator, without rubbing, to minimize any heat transfer.

Primary Outcome Measures:
    Composite Raynaud's Index (Paper Diary)

Secondary Outcome Measures:
    Improvement in global Quality of Life by SF-36
    Improvement in patient function using Scleroderma Health Assessment Questionnaire
    Reduce the net digital ulcer burden
    Prevent the emergence of new digital ulcers
    Increase healing of pre-existing digital ulcers Substudies:
    Assay of plasma 15-keto-PG levels after initial and chronic dosing
    Laser Doppler velocimetry measures during controlled cold challenge to assess effects on digital perfusion The Intent-to-Treat (ITT) Population includes all randomized subjects. The Modified Intent-to-Treat (MITT) Population includes all randomized subjects who received any amount of study drug.

The disclosure of every patent, patent application, and publication cited herein is hereby incorporated herein by reference in its entirety.

What is claimed:

1. A topical semisolid composition comprising a prostaglandin $E_1$ compound for treatment of Raynaud's phenomenon, wherein the semisolid composition comprises a total daily dose of about 0.945 mg to about 5.7 mg a prostaglandin $E_1$ compound.

2. The composition of claim 1, wherein the composition further comprises a skin penetration enhancer that is selected from:
    an N,N-di($C_1$-$C_8$) alkylamino substituted ($C_4$-$C_{18}$) alkyl ($C_2$-$C_{18}$) carboxylic ester and pharmaceutically acceptable acid addition salts thereof; and
    a ($C_1$-$C_4$)-alkyl ($C_8$-$C_{22}$) carboxylic ester.

3. The composition of claim 1, wherein the composition further comprises a thickening agent selected from a polysaccharide gum and a chemically modified polysaccharide gum.

4. The composition of claim 1, wherein the composition is stored at room temperature.

5. The composition of claim 1, wherein the composition is provided in a two-part unit dose container.

6. The composition of claim 1, wherein the composition further comprises a skin penetration enhancer that is an N,N-di($C_1$-$C_8$) alkylamino substituted ($C_4$-$C_{18}$) alkyl ($C_2$-$C_{18}$) carboxylic ester and pharmaceutically acceptable acid addition salts thereof.

7. The composition of claim 1, wherein the composition further comprises a skin penetration enhancer that is dodecyl 2-(N,N-dimethylamino)-propionate (DDAIP).

8. The composition of claim 1, wherein the composition further comprises a skin penetration enhancer that is a pharmaceutically acceptable salt of dodecyl 2-(N,N-dimethylamino)-propionate (DDAIP).

\* \* \* \* \*